United States Patent
Ek

(10) Patent No.: US 11,992,414 B2
(45) Date of Patent: May 28, 2024

(54) ARTICULAR SURFACE IMPLANTS WITH DIMPLES

(71) Applicant: Arthrosurface Incorporated, Franklin, MA (US)

(72) Inventor: Steven W. Ek, Bolton, MA (US)

(73) Assignee: Arthrosurface Incorporated, Franklin, MA (US)

(*) Notice: Subject to any disclaimer, the term of this patent is extended or adjusted under 35 U.S.C. 154(b) by 0 days.

(21) Appl. No.: 17/309,131

(22) PCT Filed: Oct. 29, 2019

(86) PCT No.: PCT/US2019/058517
§ 371 (c)(1),
(2) Date: Apr. 28, 2021

(87) PCT Pub. No.: WO2020/092335
PCT Pub. Date: May 7, 2020

(65) Prior Publication Data
US 2022/0008210 A1 Jan. 13, 2022

Related U.S. Application Data

(60) Provisional application No. 62/752,134, filed on Oct. 29, 2018.

(51) Int. Cl.
*A61F 2/38* (2006.01)
*A61F 2/30* (2006.01)

(52) U.S. Cl.
CPC ........ *A61F 2/3877* (2013.01); *A61F 2/30771* (2013.01); *A61F 2/3859* (2013.01); *A61F 2002/30125* (2013.01)

(58) Field of Classification Search
CPC .. A61F 2/3877; A61F 2/30771; A61F 2/3859; A61F 2002/30125
See application file for complete search history.

(56) References Cited

U.S. PATENT DOCUMENTS

| 4,158,894 A | 6/1979 | Worrell |
| 4,964,867 A * | 10/1990 | Boger ................. A61F 2/3877 |
| | | 623/20.18 |

(Continued)

FOREIGN PATENT DOCUMENTS

| FR | 2700260 A1 | 7/1994 |
| FR | 2833479 A1 | 6/2003 |
| WO | 1997025006 A | 7/1997 |

OTHER PUBLICATIONS

International Search Report and Written Opinion for International Patent Application No. PCT/US2019/058517 dated Jan. 16, 202, 8 pages.

(Continued)

*Primary Examiner* — Brian A Dukert
*Assistant Examiner* — Melissa A Hoban
(74) *Attorney, Agent, or Firm* — Goodwin Procter LLP

(57) ABSTRACT

An implant system for a knee comprising a femur and a patella. The implant system includes a patella implant comprising an implant body. The implant body comprises a bone facing surface, an articular facing surface, and at least one dimple. The bone facing surface engages bone beneath an implant site formed in the patella. The articular facing surface faces towards an articulating surface of the femur and has a non-anatomical shape (such as a dome). The dimples are formed in the articular facing surface and have a load bearing surface to engage against the articulating surface of the femur. The load bearing surface may have a contour that substantially corresponds to a spherical portion of a generally spherical segment or has an elongated, partially oval shape, and may be configured to increase contact area with the articulating surface of the femur, reduce stress concentrations, and increase resistance to dislocation subluxation.

20 Claims, 12 Drawing Sheets

(56) References Cited

U.S. PATENT DOCUMENTS

| | | | | |
|---|---|---|---|---|
| 5,344,458 | A | * | 9/1994 | Bonutti ............... A61F 2/30965 |
| | | | | 623/20.32 |
| 5,522,901 | A | | 6/1996 | Thomas et al. |
| 5,580,353 | A | | 12/1996 | Mendes et al. |
| 5,916,269 | A | * | 6/1999 | Serbousek ............ A61F 2/3859 |
| | | | | 623/22.24 |
| 2002/0161447 | A1 | * | 10/2002 | Salehi ................. A61F 2/30771 |
| | | | | 623/20.28 |
| 2003/0083751 | A1 | | 5/2003 | Tornier |
| 2003/0114935 | A1 | * | 6/2003 | Chan ................... A61F 2/30771 |
| | | | | 623/22.21 |
| 2003/0181984 | A1 | * | 9/2003 | Abendschein ....... A61B 17/155 |
| | | | | 623/908 |
| 2006/0009776 | A1 | * | 1/2006 | Justin ................ A61B 17/1675 |
| | | | | 606/87 |
| 2008/0133020 | A1 | * | 6/2008 | Blackwell ................. A61F 2/38 |
| | | | | 623/20.14 |
| 2008/0300689 | A1 | | 12/2008 | McKinnon et al. |
| 2014/0094820 | A1 | * | 4/2014 | Clever ............... A61B 17/1767 |
| | | | | 606/96 |
| 2019/0125541 | A1 | * | 5/2019 | Axelson, Jr. .......... A61F 2/3877 |
| 2021/0244545 | A1 | * | 8/2021 | Webb ................... A61F 2/3094 |

OTHER PUBLICATIONS

Extended European Search Report for European Patent Application No. 19880580.6 dated Jun. 28, 2023, 7 pages.

\* cited by examiner

ARTICULAR SURFACE IMPLANTS WITH DIMPLES

CROSS-REFERENCE TO RELATED APPLICATIONS

This application is a national phase filing under 35 U.S.C. § 371 of International (PCT) Patent Application No. PCT/US2019/058517, filed Oct. 29, 2019, which claims the benefit of U.S. Provisional Patent Application Ser. No. 62/752,134, filed Oct. 29, 2018, the entire disclosure of each of which is incorporated herein by reference.

FIELD

The present disclosure is related to devices and methods for the repair of defects that occur in articular cartilage on the surface of bones, and particularly to articular surface implants with dimples.

BACKGROUND

Articular cartilage, found at the ends of articulating bones in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspect of native hyaline cartilage and tends to be less durable.

In some cases, it may be necessary or desirable to repair the damaged articular cartilage using one or more implants. While implants may be successfully used, the implant should be designed to maximize the patient's comfort, minimize damage to surrounding areas, minimize potential further injury, maximize the functional life of the implant, and be easy to install.

BRIEF DESCRIPTION OF THE DRAWINGS

Features and advantages of the present invention are set forth by description of embodiments consistent with the present invention, which description should be considered in conjunction with the accompanying drawings wherein.

DETAILED DESCRIPTION

By way of an overview, one aspect of the present disclosure features systems and methods for repairing all or a portion of an articular surface associated with a bone of a joint. The joint may include any joint such as, but not limited to, a talocrural joint, a knee joint, a shoulder joint, toe joint, finger joint, or the like. As described herein, the systems and methods include an implant system for a knee comprising a femur and a patella. The implant system may include a patella implant comprising an implant body. The implant body may comprise a bone facing surface, an articular facing surface, and at least one dimple. The bone facing surface may be configured to engage bone beneath an implant site formed in the patella. The articular facing surface may be configured to face towards an articulating surface of the femur and may have a non-anatomical shape (such as a dome). The dimples may be formed in the articular facing surface and have a load bearing surface configured to engage against the articulating surface of the femur. The load bearing surface may have a contour that substantially corresponds to a spherical portion of a generally spherical segment or has an elongated, partially oval shape. The dimples may be configured to increase contact area with the articulating surface of the femur, reduce stress concentrations, and increase resistance to dislocation subluxation.

The present disclosure may therefore feature an prothesis (implant) which is particularly suited for repairing a knee joint. In particular, one or more aspects of the present disclosure may feature a patella implant. It should be appreciated that the implant described herein is not limited to the knee joint unless specifically claimed as such, and an implant consistent with one or more embodiments of the present disclosure may be installed in any joint which translates on another articular surface.

Figure 1:
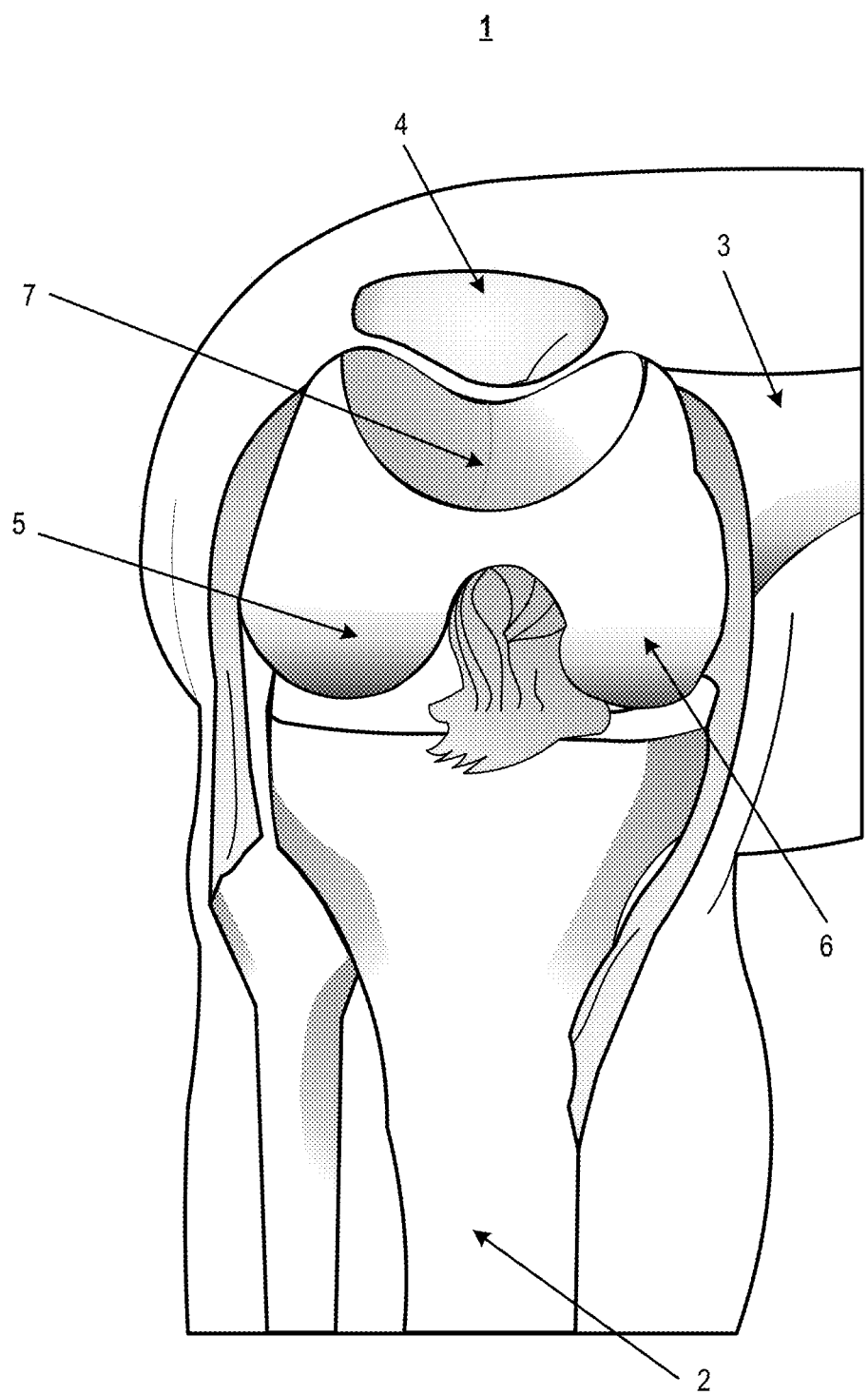
FIG. 1 generally illustrates a front view of a joint formed by a first and a second bone which the first and second implant systems may be used to repair.

Turning to FIG. 1, a diagram illustrating a knee joint 1. By way of a general overview, the knee joint 1 includes the tibia 2, the femur 3, and the patella 4 (also known as the kneecap). The femur 6 includes the lateral condyle 5, the medial condyle 6, and the trochlear groove 7. As is well understood, the tibia 2 and femur 3 articulate relative each other, and the patella 4 (which is a thick, circular-triangular bone) articulates with the femur 3 to cover and protect the anterior articular surface of the knee joint 1 (and specifically the trochlear groove 7 of the femur 3).

The patella 4 is a sesamoid bone roughly triangular in shape, with the apex of the patella 4 facing downwards towards the trochlear groove 7. The apex is the most inferior (lowest) part of the patella 4, and it is pointed in shape, and gives attachment to the patellar ligament. The front and back surfaces of the patella 4 are joined by a thin margin and towards center by a thicker margin. The tendon of the quadriceps femoris muscle attaches to the base of the patella 4, with the vastus intermedius muscle attaching to the base itself, and the vastus lateralis and vastus medialis are attached to outer lateral and medial borders of patella 4 respectively.

The upper third of the front of the patella 4 is coarse, flattened, and rough, and serves for the attachment of the tendon of the quadriceps. The middle third has numerous vascular canaliculi. The lower third culminates in the apex which serves as the origin of the patellar ligament. The posterior surface is divided into two parts. The upper three-quarters of the patella 13 articulates with the femur 3 (e.g., with the trochlear groove 7) and is subdivided into a medial and a lateral facet by a vertical ledge which varies in shape. In human adults, the articular surface of the patella 4 may be about 12 cm$^2$ (1.9 sq. in) and covered by cartilage, which may reach a maximal thickness of about 6 mm (0.24 in) in the center at about 30 years of age. The lower part of the posterior surface of the patella 4 has vascular canaliculi filled and is filled by fatty tissue (i.e., the infrapatellar fat pad).

Due to the great stress on the patellofemoral joint 1 during resisted knee flexion, damage to the patellofemoral joint 1 is common. In many situations, the anterior articular surface of the femur 3 (e.g., the trochlear groove 7) and/or the articular surface of the patella 4 may become damaged and/or need to be replaced. There are several known implants for repairing all or a portion of the lateral condyle 5, the medial condyle 6, and/or the trochlear groove 7. One such example of an implant for repairing trochlear groove 7 is described in U.S. Pat. No. 8,388,624, which is fully incorporated herein by reference. It should be understood, however, that the implants described herein (e.g., patella implants) are not limited to being used in combination this particular trochlear groove implant unless specifically claimed as such. To this end, the implants described herein (e.g., patella implants) may articulate against a patient's native articular cartilage.

Figure 2:
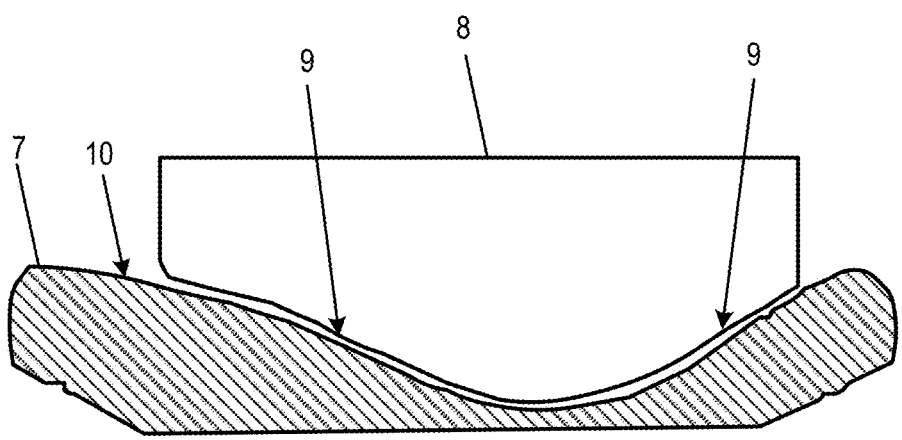
FIG. 2 generally illustrates a schematic example of an anatomical patella implant.

At least two different types of patella implants exist, namely, anatomical patella implants and dome patella implants. One schematic example of an anatomical patella implant 8 is generally illustrated in FIG. 2. In general, an anatomical patella implant 8 may include an articular surface 9 having contour that substantially corresponds to (e.g., approximates) the original anatomical articular surface contour of the patient's patella and/or trochlear groove 7. For example, an anatomical patella implant 8 may be based on a plurality of measurements of the patient's native patella 4 and/or trochlear groove 7 and have a roughly triangular shape subdivided into a medial and a lateral facet by a vertical ledge and are intended to mimic the original anatomical contour of the patient's patella 4 and/or trochlear groove 7. As can be seen, the contour of the articular surface 9 of an anatomical patella implant 8 may closely follow the contour of the articular surface 10 of the trochlear groove 7, thereby resulting in a large contact area with the trochlear groove 7. The large contact area between the anatomical patella implant 8 and the trochlear groove 7 may result in reduced the stress concentrations between the anatomical patella implant 8 and the trochlear groove 7. The increased contact area and reduced stresses of anatomical patella implants may also reduce the likelihood of dislocation and/or subluxation of the patella and/or premature wear of the articulating surfaces 9, 10. In particular, the most common type of subluxation of the patella 4 is lateral subluxation in which the patella 4 moves laterally towards the outside of the trochlear groove 7.

Figure 3:
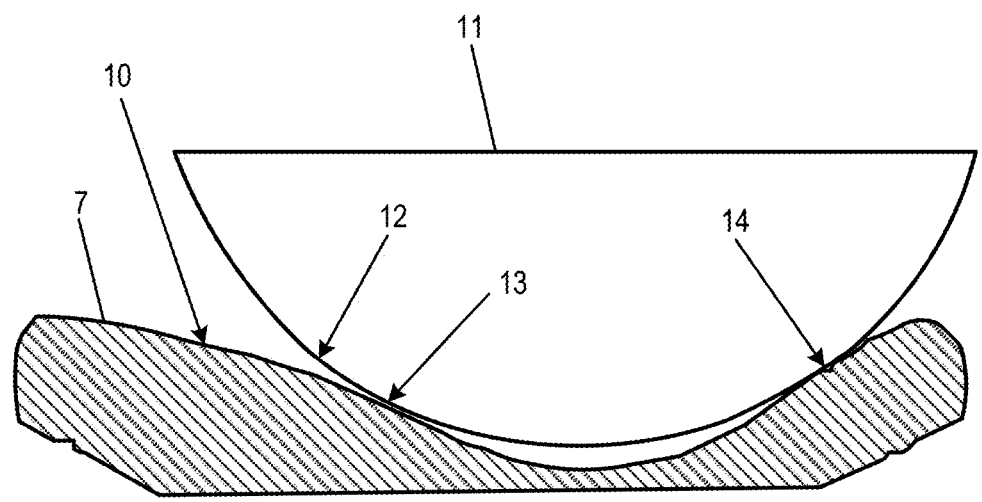
FIG. 3 generally illustrates a schematic example of a dome patella implant.
Figure 4:
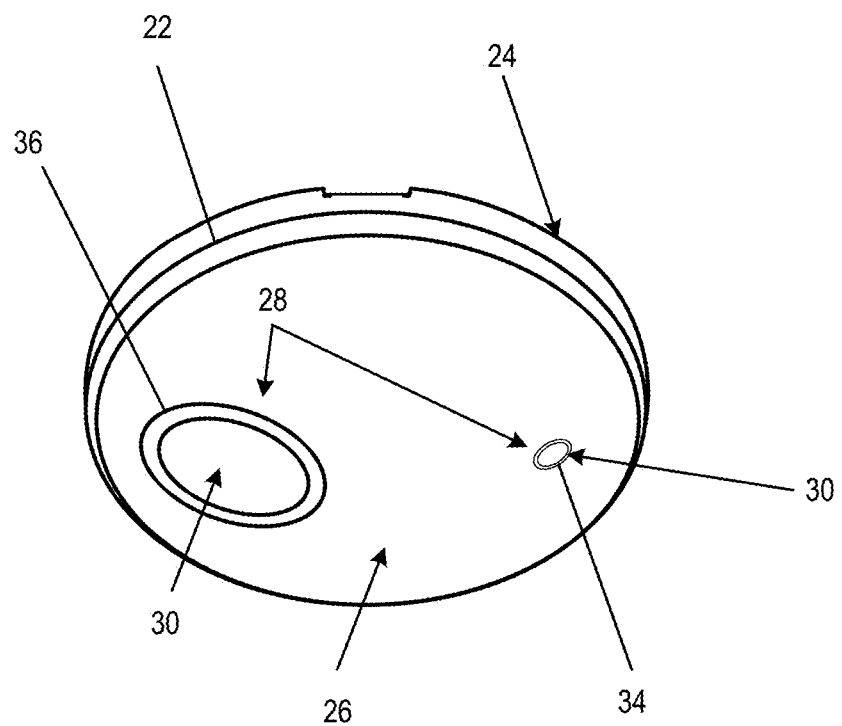
FIG. 4 generally illustrates is a top, front perspective view of one aspect of an implant consistent with the present disclosure.

One schematic example of a dome patella implant 11 is generally illustrated in FIG. 3. A dome patella implant 11 may include an articular surface 12 generally in the shape of a spherical segment (e.g., dome shape). The dome shape is not intended to approximate the original anatomical contour of the patient's patella 4 and/or trochlear groove 7. Whereas anatomical patella implants 8 may be uniquely contoured for each patient, dome patella implants 11 are provided in a range of sizes and shapes, and the best fit size and shape is used. One benefit of dome patella implants 11 compared to anatomical patella implants 8 is that dome patella implants 11 are easier to install compared to anatomical patella implants 8. For example, in order for anatomical patella implants 8 to function properly, anatomical patella implants 8 may need to be precisely installed onto the patient's patella 4. If anatomical patella implants 8 are slightly misaligned, then anatomical patella implants 8 may not articulate properly on the articular surface 10 of the trochlear groove 7, thereby increasing the possibility of damage to the anatomical patella implant 8 and/or the cooperating articular surface 10 of the trochlear groove 7, causing further patient discomfort/pain, as well as increasing the possibility of future subluxation. In contrast, because dome patella implants 11 may have an articular surface 12 generally in the shape of a spherical segment, these implants 11 are generally symmetrical. As such, dome patella implants 11 may not have a specific orientation relative to the patient's patella 4 and/or trochlear groove 7.

Unfortunately, dome patella implants 11 also have some potential disadvantages compared to anatomical patella implants 8. For example, a dome patella implant 11 may generally have only two points 13, 14 of contact with the articular surface 10 of the trochlear groove 7 due to the generally spherical shape of the articular surface 12 of the dome patella implant 11. As a result, the contact area between the dome patella implant 11 and the trochlear groove 7 (e.g., the two points 13, 14) may be much smaller compared to an anatomical patella implant 8 and/or the native knee joint. The relatively small contact areas 13, 14 may increase the stress concentration on the dome patella implant 11 and/or the trochlear groove 7 which can result in debris being generated. This debris may cause patient irritation and/or pain, and may result if further damage to the articulating surfaces of the knee joint 1. Moreover, the relatively small contact areas 13, 14 may increase the likelihood of possibility of future subluxation compared to anatomical patella implants 8.

Therefore, what is needed is an implant (e.g., a patella implant) which is easier to install than an anatomical patella implant, but which has a greater contact area with the trochlear groove, thereby resulting in reduced stress concentrations and being more resistant to subluxation compared to dome patella implants.

Turning now to FIGS. 4-9, one example of an implant 20 consistent with at least one aspect of the present disclosure is generally illustrated. In particular, FIG. 4 generally illustrates is a top, front perspective view of the implant 20, FIG. 5 generally illustrates a top view of the implant 20, FIG. 6 generally illustrates a top, rear perspective view of the implant 20, FIG. 7 generally illustrates a bottom view of the implant 20 and trochlear groove 21, FIG. 8 generally illustrates an exploded view of the implant 20 and trochlear groove 21, and FIG. 9 generally illustrates an assembled view of the implant 20 coupled to the patella 4 and articulating against the articular surface 23 of the trochlear groove 21. While various aspects of the implant 20 may be described in the context of a patella implant configured to articulate against an articular surface 23 of the trochlear groove 21, it should be appreciated that implants 20 consistent with the present disclosure are not limited to patella implants unless specifically claimed as such. In addition, it should be appreciated that the articular surface 23 of the trochlear groove 21 against which the implant 20 articulates against may include a patient's native articular cartilage and/or a replacement articular surface (i.e., the articular surface of a knee implant). The knee implant may include a total knee implant and/or a partial knee implant (such as, but not limited to, a trochlear groove implant as generally described in U.S. Pat. No. 8,388,624, which is fully incorporated herein by reference).

The patella implant 20 may include an implant body 22 having a bone facing surface 24, an articular facing surface 26, and one or more dimples 28. The implant body 22 may include a one-piece implant body or a multi-piece implant body. For example, the one-piece implant body 22 may include a monolithic structure and the multi-piece implant body 22 may include a mounting component having the bone facing surface 24 configured to be secured to the patient's patella bone and an articulating component having the articular facing surface 26. The implant body 22, or a portion thereof, may be manufactured from metal (such as, but not limited to, chromium alloys, titanium alloys, stainless steel alloys, or the like), from plastic (such as, but not limited to, polyethylene based plastics) and/or ceramics.

The bone facing surface 24 of the implant body 22 may be configured to be secured to, coupled to, mounted to, and/or otherwise engage against at least a portion of the bone within an implant site formed in the patient's patella bone. According to one aspect, the implant site may be formed by making one or more planar cuts in the patient's patella bone. The bone facing surface 24 of the implant body 22 may optionally have a contour that substantially matches and/or corresponds to the resulting contour of the patient's patella bone.

Alternatively, the implant site may have a size and shape configured to generally correspond to and receive at least a portion of the bone facing surface 24 of the implant body 22. For example, the perimeter of the implant body 22 (e.g., the transitional area between the bone facing surface 24 and the articular facing surface 26) may abut against (e.g., continuously abut against) a remaining portion of the patient's patella bone. According to one aspect, the implant site may be formed by one or more reamers rotated about a cutting axis, for example, as generally described in U.S. Pat. Nos. 7,678,151 and/or 8,361,159 (both of which are fully incorporated by reference) and/or by robotically (e.g., using a multi-axis computer numerical control (CNC) machine). Optionally, the bone facing surface 24 may have a contour that is revolved around the cutting axis, though this is not a limitation of the present disclosure unless specifically claimed as such.

Figure 7:
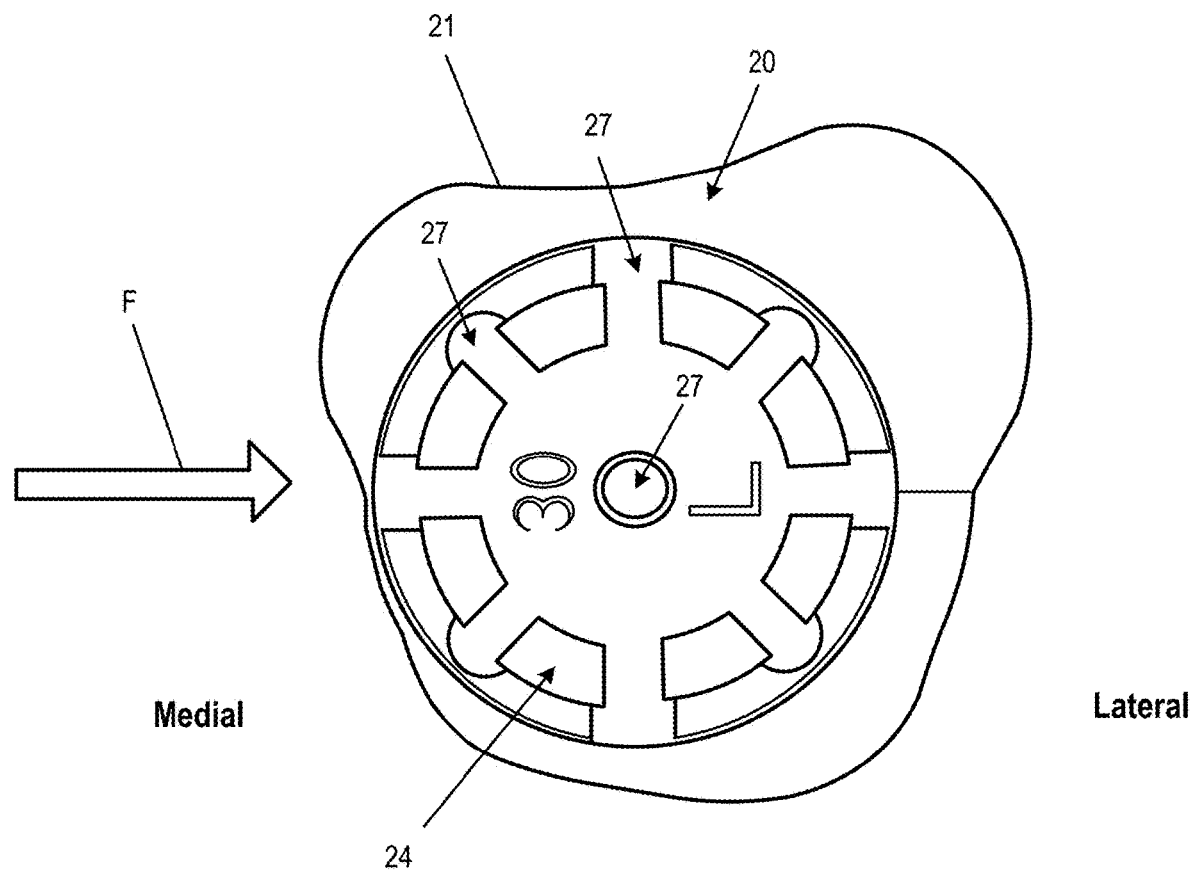
FIG. 7 generally illustrates a bottom view of the implant of FIG. 4 and trochlear groove.
Figure 8:
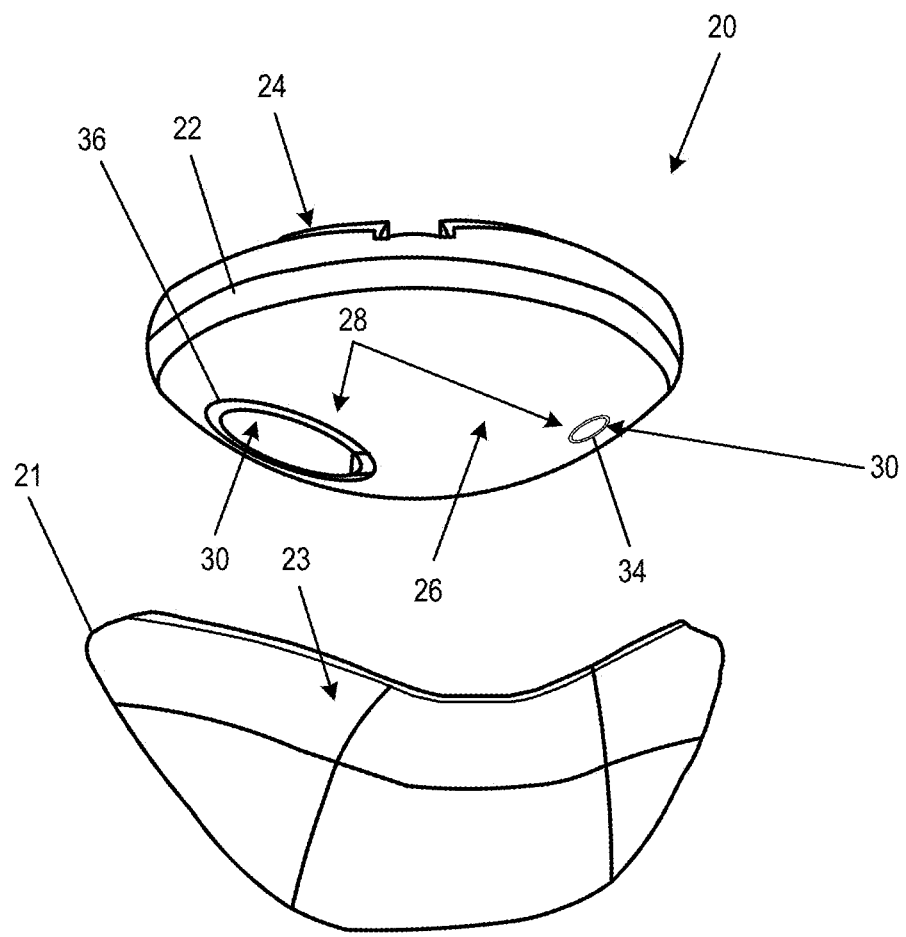
FIG. 8 generally illustrates an exploded view of the implant of FIG. 4 and trochlear groove.
Figure 9:
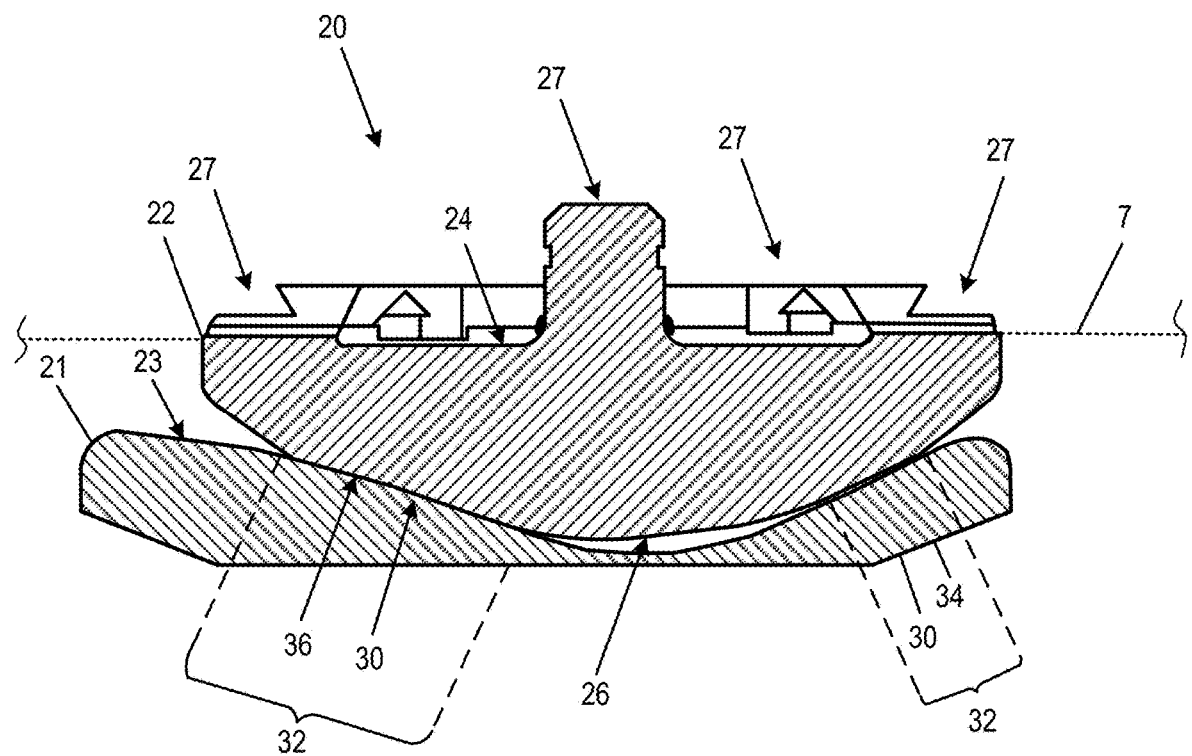
FIG. 9 generally illustrates an assembled view of the implant of FIG. 4 coupled to the patella and articulating against the articular surface of the trochlear groove.
Figure 10:
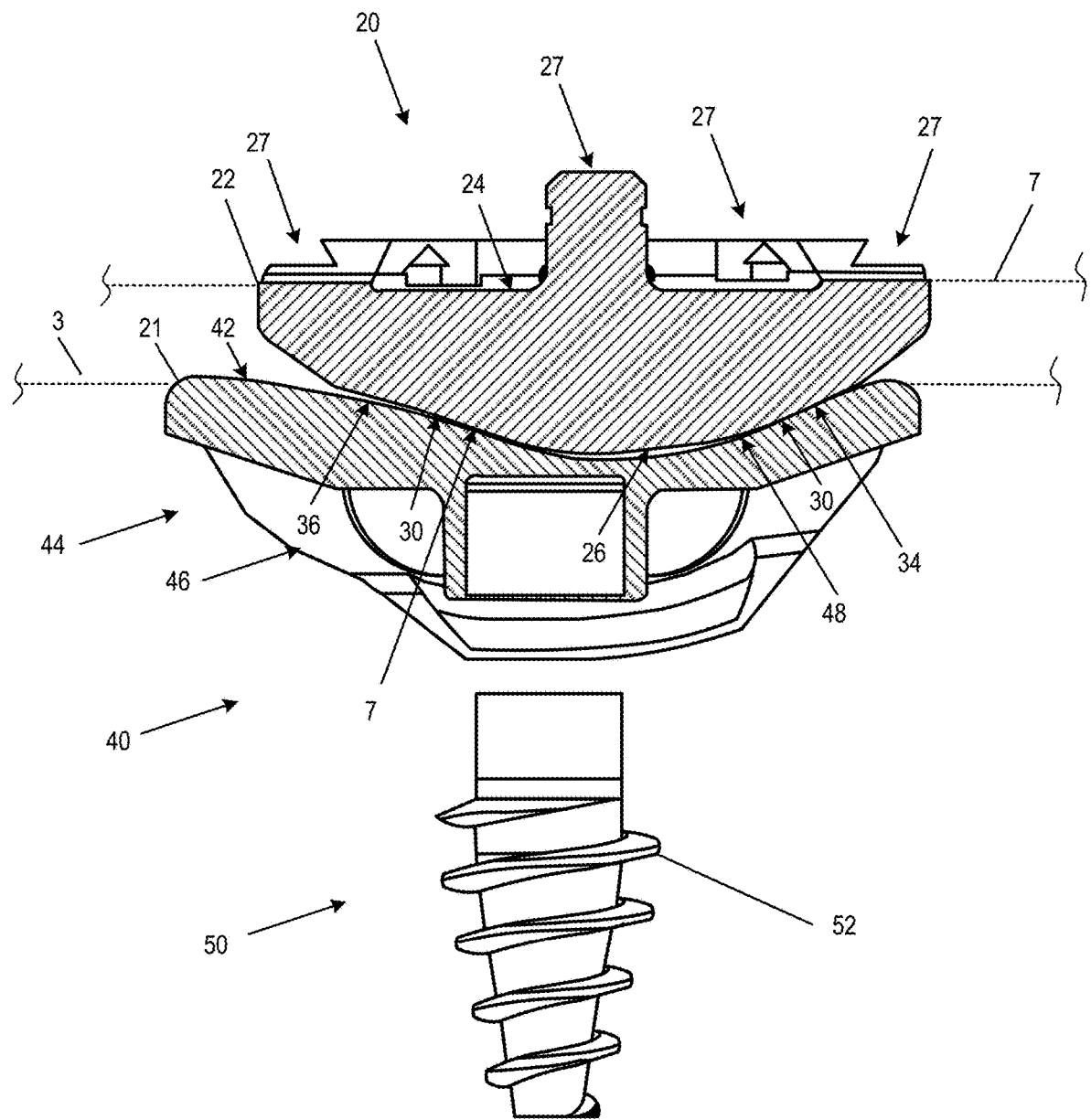
FIG. 10 generally illustrates an assembled view of the implant of FIG. 4 coupled to the patella and articulating against the articular surface of a trochlear groove implant.
Figure 11:
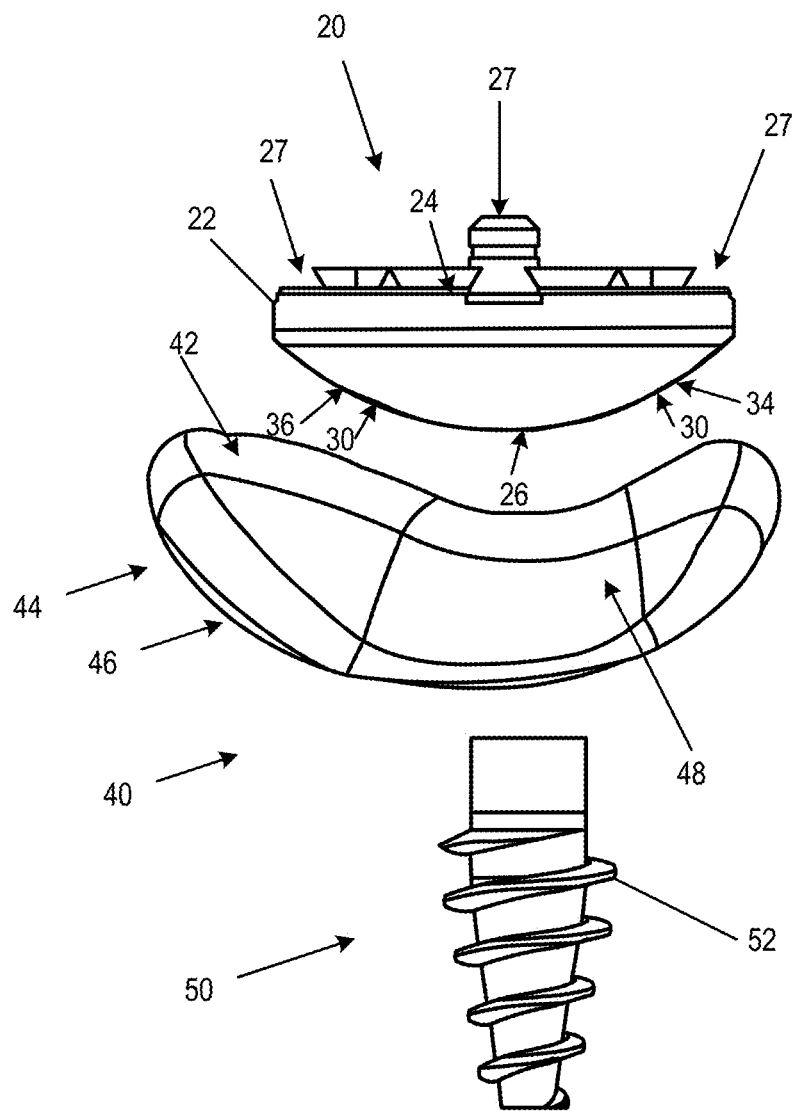
FIG. 11 generally illustrates an exploded view of the implant of FIG. 4 and the trochlear groove implant of FIG. 10.
Figure 12:
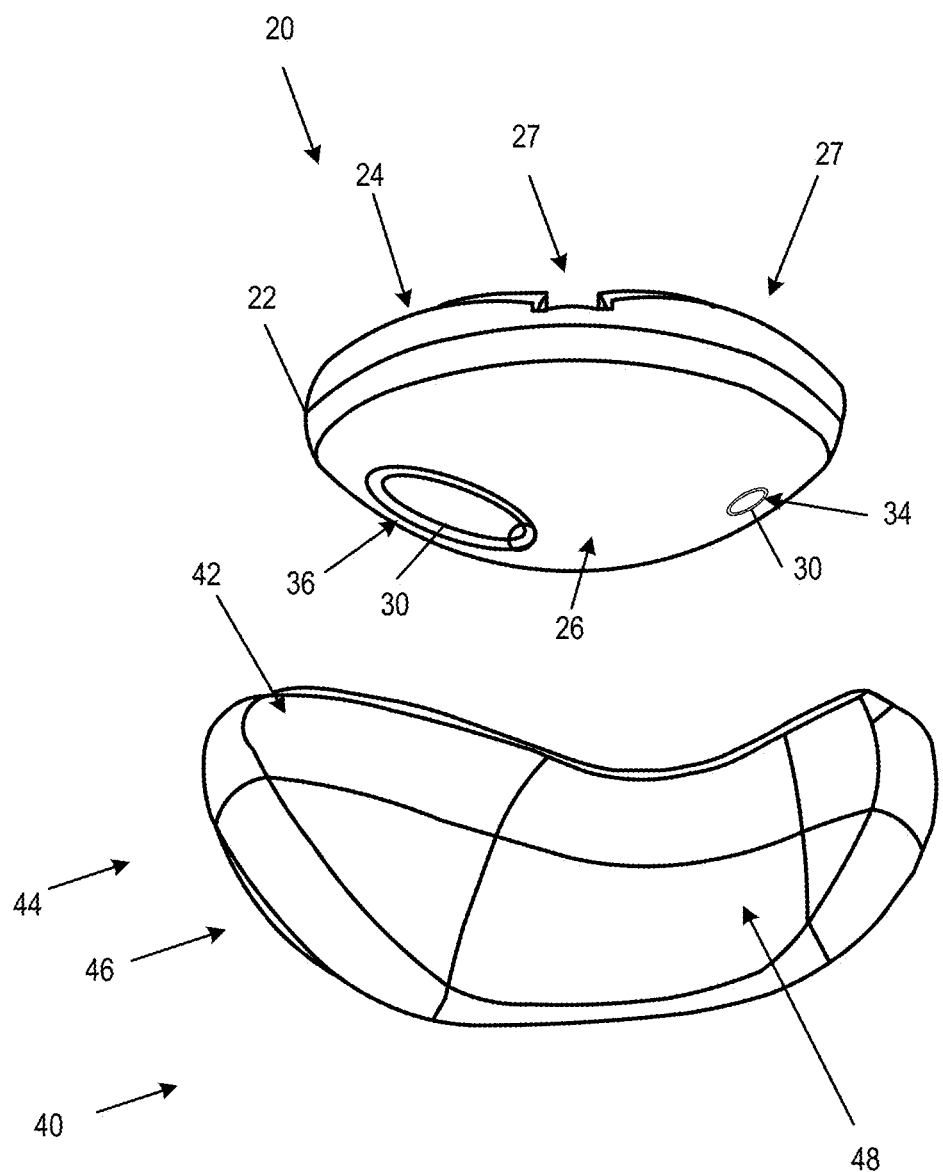
FIG. 12 generally illustrates another exploded view of the implant of FIG. 4 and the trochlear groove implant of FIG. 10.
Figure 13:
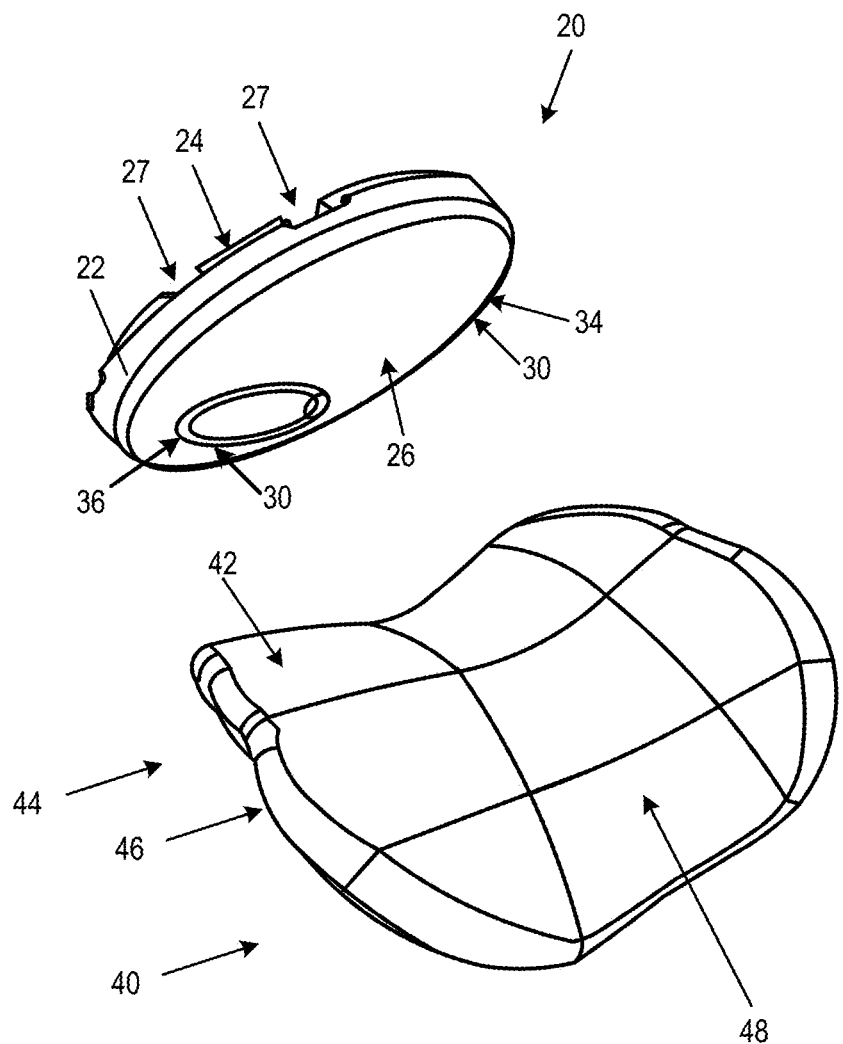
FIG. 13 generally illustrates a further exploded view of the implant of FIG. 4 and the trochlear groove implant of FIG. 10.

The bone facing surface 24 of the implant body 22 may be secured to the bone 7 within the implant site using any mechanism known to those skilled in the art. For example, the bone facing surface 24 of the implant body 22 may be secured to the bone 7 using bone cement, one or more pegs, hooks, protrusions, ribs, cut-outs, screws, anchors, and/or the like 27 (FIGS. 7 and 9). Optionally, the bone facing surface 24 of the implant body 22 may be treated and/or include a material configured to promote bone regrowth and/or regrowth of the patient's native articular cartilage.

The articular facing surface 26 may be configured to face towards patient's trochlear groove when the patella implant 20 is installed in the implant site on the patient's patella bone. The articular facing surface 26 may have a non-anatomical shape. According to one aspect, the non-anatomical shape may be a dome shape. For example, the dome shape may have a contour that substantially corresponds to a spherical portion of a generally spherical segment. As used herein, the phrase "generally spherical segment" means that the radius varies no more than 15% across at least 60% of the articular facing surface 26. Alternatively (or in addition), the dome shape may have an elongated, partially oval shape. The articular facing surface 26 may optionally articulate against a portion of the articulating surface 23 of the trochlear groove 21 (i.e., the patient's native articular cartilage and/or trochlear groove implant).

The patella implant 20 may be configured to be received within an implant site such that the articular facing surface 26 is disposed substantially where the patient's removed native cartilage was originally located. In at least one example, the patella implant 20 may be configured to be received within an implant site such that the articular facing surface 26 is substantially continuous with the patient's native cartilage surrounding the implant site. Put another way, the patella implant 20 may be configured to be received within an implant site such that the articular facing surface 26 is substantially flush with the patient's native cartilage surrounding the implant site. Alternatively (or in addition), the patient's native cartilage may be completely removed.

As noted herein, the patella implant 20 may also include one or more dimples 28. The dimples 28 may include one or more areas that are recessed relative to the articular facing surface 26. At least a portion of the dimples 28 may include a load bearing surface 30 configured to articulate against a portion of the articulating surface 23 of the trochlear groove 21 (i.e., the patient's native articular cartilage and/or trochlear groove implant). The load bearing surface 30 of one or more of the dimples 28 may have a contour that substantially corresponds to a spherical portion of a generally spherical segment. Alternatively (or in addition), load bearing surface 30 of one or more of the dimples 28 may have an elongated, partially oval shape. For example, the long axis of the elongated, partially oval shaped dimples 28 may extend generally in the primary direction that the patella implant 20 moves relative to the articulating surface 23 of the trochlear groove 21.

As best seen in FIG. 9, the dimples 28 may increase the surface contact area 32 between the patella implant 20 and the articulating surface 23 of the trochlear groove 21 compared to the known dome patella implants. This increased surface contact area 32 of the patella implant 20 may reduce the stress concentration between the patella implant 20 and the articulating surface 23 of the trochlear groove 21 compared to known dome patella implants, thereby decreasing wear of the patella implant 20 and/or the articulating surface 23 of the trochlear groove 21. The reduced wear may increase the lifespan of patella implant 20 and/or trochlear groove implant. Moreover, the reduced wear may reduce and/or eliminate the creation of debris, which can cause patient discomfort and/or premature wear of the articulating surfaces within the knee joint 1.

In addition, the increased surface contact area 32 of the patella implant 20 may increase the resistance of the patella implant 20 to dislocation forces (e.g., lateral dislocation force F as generally illustrated in FIG. 7) compared to known dome patella implants. To this end, the contour and/or position of the dimples 28 within the patella implant 20 relative to the articulating surface 23 of the trochlear groove 21 may aid in preventing dislocation of the patella implant 20 as the patella implant 20 moves along the articulating surface 23 of the trochlear groove 21.

One or more of the dimples 28 may include a medial dimple 34 configured to articulate against the medial facet of the trochlear groove 21. Alternatively (or in addition), one or more of the dimples 28 may include a lateral dimple 36 configured to articulate against the lateral facet of the trochlear groove 21. The size, shape, and contour of the medial dimples 34 and/or lateral dimples 36 may be configured to engage the medial and/or lateral facets of the trochlear groove 21, respectively, to further increase the resistance to dislocation forces. According to one aspect, the depth and/or contour of the medial dimples 34 and/or lateral dimples 36 may be based on a general (e.g., generic) anatomical model of the medial and/or lateral facets of the trochlear groove 21 such that the load bearing surfaces 30 of the dimples closely resembles the articulating surface 23 of the trochlear groove 21, thereby increasing the surface contact area 32 of the patella implant 20. In the illustrated example, the area of the load bearing surface 30 of the lateral dimple 36 may be larger than the area of the load bearing surface 30 of the medial dimple 34, though this is not a limitation of the present disclosure unless specifically claimed as such. For example, the area of the load bearing surface 30 of the lateral dimple 36 may be at least 50% greater than the area of the load bearing surface 30 of the medial dimple 34, the area of the load bearing surface 30 of the lateral dimple 36 may be at least 75% greater than the area of the load bearing surface 30 of the medial dimple 34, the area of the load bearing surface 30 of the lateral dimple 36 may be at least 100% greater than the area of the load bearing surface 30 of the medial dimple 34, the area of the load bearing surface 30 of the lateral dimple 36 may be at least 150% greater than the area of the load bearing surface 30 of the medial dimple 34, the area of the load bearing surface 30 of the lateral dimple 36 may be at least 200% greater than the area of the load bearing surface 30 of the medial dimple 34, and/or the area of the load bearing surface 30 of the lateral dimple 36 may be at least 300% greater than the area of the load bearing surface 30 of the medial dimple 34, including all values and ranges therein.

The load bearing surface 30 of one or more of the dimples 28 may be formed from a different material than the implant body 22 and/or the articular facing surface 26. For example, the load bearing surface 30 may be made from a material having a very low coefficient of friction, self-lubricating; and/or is highly resistant to abrasion such as, but not limited to, ultra-high-molecular-weight polyethylene (UHMWPE) or the like. Alternatively, load bearing surface 30 of the dimples 28 may be formed from the same material as the implant body 22 and/or the articular facing surface 26.

Figure 5:
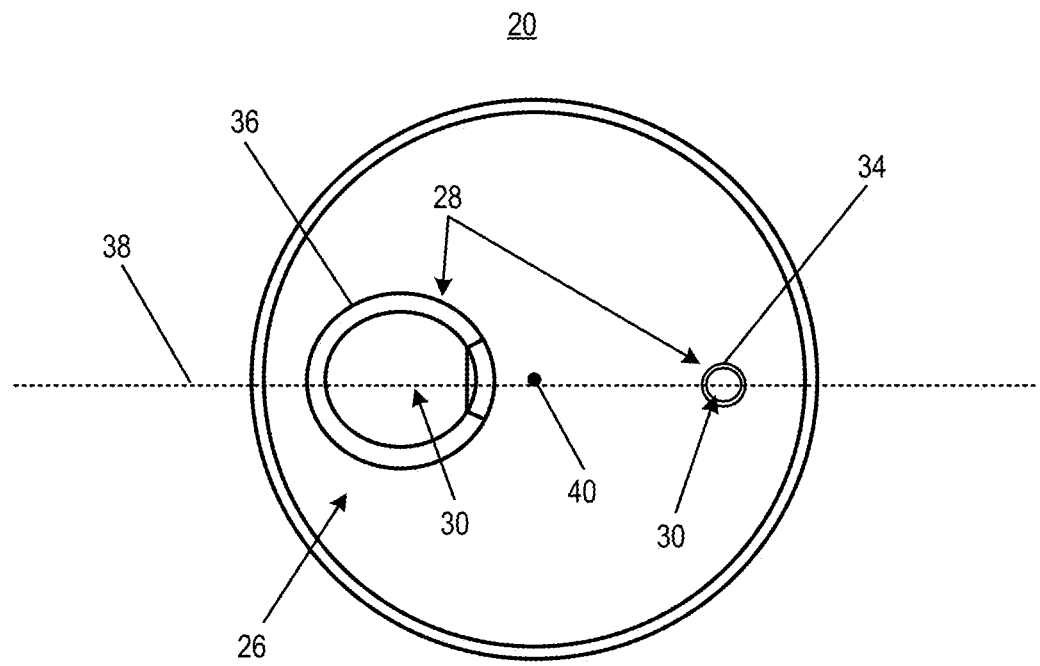
FIG. 5 generally illustrates a top view of the implant of FIG. 4.
Figure 6:
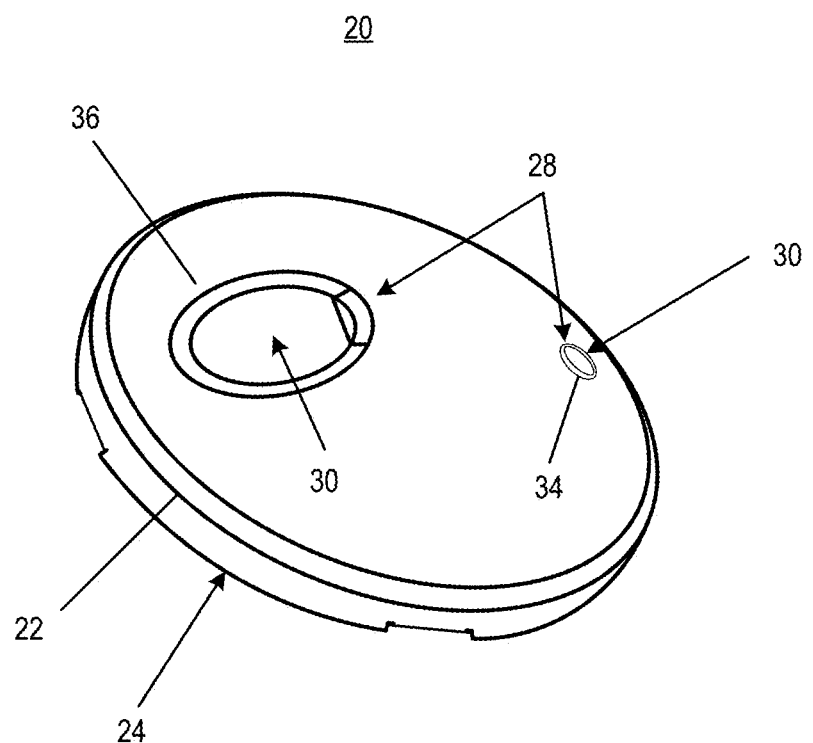
FIG. 6 generally illustrates a top, rear perspective view of the implant of FIG. 4.

Two or more dimples 28 (e.g., one or more of the medial dimples 34 and/or lateral dimples 36) may be located on generally opposite side of the patella implant 20, e.g., as generally illustrated in FIG. 5. According to one aspect, the plurality of dimples 28 may be located at least partially along at least one common plane 38. The common plane 38 may extend through a center and/or central region 40 of the patella implant 20 (e.g., the center of the articular facing surface 26). Optionally, the common plane 38 may extend generally transverse and/or perpendicular to the direction of movement of the patella implant 20 relative to the articulating surface 23 of the trochlear groove 21. Alternatively (or in addition), the common plane 38 may not extend through the center 40 of the patella implant 20. For example, a plurality of dimples 28 may be arranged along a common plane 38 that extend generally in the direction of movement of the patella implant 20 relative to the articulating surface 23 of the trochlear groove 21.

As discussed herein, the articular surface 23 of the trochlear groove 21 against which the patella implant 20 articulates against may include a patient's native articular cartilage and/or a replacement articular surface (i.e., the articular surface of a knee implant). The replacement articular surface may include an implant as described in U.S. Pat. Nos. 7,678,151 and/or 8,361,159 (both of which are fully incorporated by reference). Alternatively (or in addition), the replacement articular surface may include a trochlear groove implant 40 may include a trochlear groove implant as generally described in U.S. Pat. No. 8,388,624, which is fully incorporated herein by reference. One example of a trochlear groove implant 40 which may articulate against a patella implant 20 consistent with at least one aspect of the present disclosure is generally illustrated in FIGS. 10-13.

In particular, the articulating surface 23 of the trochlear groove 21 may include a load bearing surface 42 of a trochlear groove implant 40. The trochlear groove implant 40 may include any trochlear groove implant generally described in U.S. Pat. No. 8,388,624, which is fully incorporated herein by reference. The trochlear groove implant 40 may include a trochlear groove implant body 44 configured to be secured to the bone of the femur 3. For example, the trochlear groove implant 40 may be configured to be secured to the femur 3 and replace at least a portion of the trochlear groove 7.

The trochlear groove implant body 44 may include a bone facing surface 46 and a load bearing surface 48. The bone facing surface 46 of the trochlear groove implant body 44 may be secured to the bone 3 within an implant site using any mechanism known to those skilled in the art. For example, the bone facing surface 46 may be secured to the bone 3 using bone cement, one or more pegs, hooks, protrusions, ribs, cut-outs, screws, anchors, and/or the like 50. In the illustrated embodiment, the bone facing surface 46 may be secured to the bone 3 using a screw, post, or peg 50 which may be a separate component from the trochlear groove implant body 44. The anchor 50 may optionally include one or more threads, ribs, or the like 52 and may be coupled (e.g., removably coupled) to the trochlear groove implant body 44 using a friction fit connection and/or a positive mechanical engagement therebetween. A friction fit may be understood herein as a connection that relies upon friction to inhibit separation of the parts, particularly one where one part is compressed (deformed) against the other. A positive mechanical engagement may be understood as a connection formed between the components that relies upon mechanical engagement and interlocking of the parts to inhibit separation (such as the use of overlapping surfaces, cotter pins passing through the connector and anchor base, set screws, etc.).

The load bearing surface 48 may be configured to face towards patella implant 20 when installed in the implant site on the femur 3. The load bearing surface 48 may have an anatomical and/or a non-anatomical shape. The trochlear groove implant 40 may be configured to be received within an implant site in the femur 3 such that the load bearing surface 48 is disposed substantially where the patient's removed native cartilage was originally located. In at least one example, the trochlear groove implant 40 may be configured to be received within an implant site such that the load bearing surface 48 is substantially continuous with the patient's native cartilage surrounding the implant site. Put another way, the trochlear groove implant 40 may be configured to be received within an implant site such that the load bearing surface 48 is substantially flush with the patient's native cartilage surrounding the implant site. Alternatively (or in addition), the patient's native cartilage may be completely removed.

It should be appreciated that one or more aspects of the patella implants described herein are easier to install than the known anatomical patella implants. In particular, the dimples do not need to be as accurately aligned known anatomical patella implants, and the installation process is similar to the known dome patella implants. Moreover, the dimples greatly increase the contact area between the patella implant and the articulating surface of the trochlear groove compared to the known dome patella implant. This increased contact area results in reduced stress concentrations and being more resistant to subluxation compared to known dome patella implants.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims.

What is claimed:

1. An implant system for a knee comprising a femur and a patella, said implant system comprising:
   a patella implant comprising:
      an implant body including:
         a bone facing surface configured to engage bone beneath an implant site formed in said patella;
         an articular facing surface configured to face towards an articulating surface of said femur, said articular facing surface having a non-anatomical shape; and
   a first and second dimple each being formed in said articular facing surface, said first and second dimple each having a load bearing surface configured to engage against said articulating surface of said femur, so as to increase a contact area between the articulating facing surface and the articulating surface of said femur; wherein said first dimple comprises a medial dimple and said second dimple comprises a lateral dimple configured to articulate against a medial facet and a lateral facet, respectively, of a trochlear groove of said femur, and wherein an area of said load bearing surface of said lateral dimple is larger than an area of said load bearing surface of said medial dimple, wherein said medial dimple and said lateral dimple are aligned along a common plane, wherein said common plane extends through a central region of said patella implant, wherein said common plane extends perpendicular to a direction of movement of said patella implant relative to said articulating surface of said femur, wherein at least one of said load bearing surface of said first and second dimple has a contour having a spherical dome shaped indentation and wherein at least one of said load bearing surface of said first and second dimple has a circular or an elongated oval shape.

2. The implant system of claim 1, wherein a long axis of said at least one of said elongated oval shaped dimples extends in a primary direction such that said patella implant moves relative to said articulating surface of said femur.

3. The implant system of claim 1, wherein said non-anatomical shape comprises a dome.

4. The implant system of claim 3, wherein said dome has an articulating facing surface contour that corresponds to a spherical portion of a spherical segment.

5. The implant system of claim 3, wherein said dome has an elongated, partially oval shape.

6. The implant system of claim 1, wherein said articulating surface of said femur comprises articular cartilage.

7. The implant system of claim 1, wherein said articulating surface of said femur comprises a trochlear groove implant.

8. The implant system of claim 1, wherein said implant body comprises a plastic.

9. The implant system of claim 8, wherein the load bearing surface of at least one of the first dimple and the second dimple comprise ultra-high-molecular-weight polyethylene (UHMWPE).

10. The implant system of claim 1, wherein said bone facing surface has a surface contour revolved around a central axis.

11. The implant system of claim 10, further comprising a peg extending outwardly from said bone facing surface along said central axis.

12. The implant system of claim 1, wherein said patella implant is configured to contact said articulating surface of said femur only at one or both of said load bearing surfaces of said first and second dimple.

13. The implant system of claim 1, wherein the area of the load bearing surface of the lateral dimple is at least 50% greater than the area of the load bearing surface of the medial dimple.

14. The implant system of claim 13, wherein the area of the load bearing surface of the lateral dimple is at least 75% greater than the area of the load bearing surface of the medial dimple.

15. The implant system of claim 14, wherein the area of the load bearing surface of the lateral dimple is at least 100% greater than the area of the load bearing surface of the medial dimple.

16. The implant system of claim 15, wherein the area of the load bearing surface of the lateral dimple is at least 150% greater than the area of the load bearing surface of the medial dimple.

17. The implant system of claim 16, wherein the area of the load bearing surface of the lateral dimple is at least 200% greater than the area of the load bearing surface of the medial dimple.

18. The implant system of claim 17, wherein the area of the load bearing surface of the lateral dimple is at least 300% greater than the area of the load bearing surface of the medial dimple.

19. The implant system of claim 1, wherein the bone facing surface further comprises at least one selected from the group consisting of a peg, a hook, a protrusion, a rib, a cut-out, a screw, an anchor, or any combination thereof.

20. The implant system of claim 1, wherein the bone facing surface is treated with or comprises a material adapted to promote bone regrowth or regrowth of a patient's native articular cartilage.

* * * * *